United States Patent
Kahl

[11] Patent Number: 5,245,857
[45] Date of Patent: Sep. 21, 1993

[54] CONTINUOUSLY OPERATED GAS ANALYZER

[75] Inventor: Melchior Kahl, Bayerwerk, Fed. Rep. of Germany

[73] Assignee: Bayer Aktiengesellschaft, Leverkusen, Fed. Rep. of Germany

[21] Appl. No.: 869,688

[22] Filed: Apr. 16, 1992

[30] Foreign Application Priority Data

Apr. 26, 1991 [DE] Fed. Rep. of Germany ....... 4113695

[51] Int. Cl.$^5$ ............................................ G01N 27/16
[52] U.S. Cl. .................................................. 73/23.2
[58] Field of Search ...................................... 73/23.2

[56] References Cited

U.S. PATENT DOCUMENTS

| 4,341,108 | 7/1982 | Warncke et al. | 73/23.2 |
| 4,379,402 | 4/1983 | Harmann, III | 73/23.2 X |

Primary Examiner—Hezron Williams
Assistant Examiner—Joseph W. Roskos
Attorney, Agent, or Firm—Sprung Horn Kramer & Woods

[57] ABSTRACT

The gas analyzer comprises a detector (3) which is dependent upon the mass flow, with a suction device (4) at the detector output. The detector output is connected to a vacuum regulating circuit (6) which maintains the vacuum constant, generated by the suction device (4), at the detector output in relation to the atmospheric pressure. The detector (3) is preceded by a choke (2) in the pipe-line for the gas to be measured. A second choke (11) is connected in parallel, by way of by-pass, to the series arrangement of the first choke (2) and the detector (3). A further (third) choke (1) is connected in advance of the common gas inlet (12, 13). A second vacuum regulating circuit (14) is connected to the common connection point and maintains the pressure constant, prevailing at said connection point, in relation to the atmospheric pressure. The two vacuum regulating circuits (6, 14) each comprise a piezoelectric pressure sensor (18a, 18b), a proportional/Integral controller (20a, 20b) and an electropneumatic control element (21a, 21b).

1 Claim, 1 Drawing Sheet

CONTINUOUSLY OPERATED GAS ANALYZER

BACKGROUND OF THE INVENTION

The invention relates to a continuously operated gas analyser comprising:

a) a detector which is dependent upon the mass flow of the gas to be analyzed, b) a suction device at the detector output, c) a vacuum regulating circuit which is connected to the detector output and which maintains constant the vacuum $p_3$, generated by the suction device, at the detector output in relation to the atmospheric pressure $p_o$, d) a first choke which is connected in advance of the detector in the pipe-line for the gas to be measured, e) a second choke which is connected in parallel to the series arrangement of the first choke and the detector as a by-pass, f) a third choke which is connected in advance of the common gas inlet and g) a further vacuum regulating circuit which is connected to the common connection point of the three chokes and which maintains constant the pressure $p_2$ prevailing at said connection point in relation to the atmospheric pressure $p_o$.

A gas analyser of this type which is operated under vacuum and is equipped with regulating circuits is described in U.S. Pat. No. 4,341,108. However, it has been established that the vacuum regulation requires improvement if more stringent demands are imposed on the measurement accuracy.

SUMMARY OF THE INVENTION

Therefore the aim of the invention is to improve the regulating accuracy of the vacuum regulation performed in the previously described, continuously operated gas analyser.

This aim is fulfilled, in accordance with the invention, in that the vacuum regulating circuits each comprise a piezoelectric pressure sensor, a PI-controller and an electropneumatic control element.

By virtue of the combination of the piezoelectric pressure sensor with a PI-controller and an electropneumatic control element it is possible to improve the reproducibility, the temperature dependence and the long-term stability of the apparatus by approximately one power of ten.

BRIEF DESCRIPTION OF THE DRAWING

The single FIGURE is a schematic diagram of a continuously operated gas analyser in accordance with the present invention.

DESCRIPTION OF THE PREFERRED EMBODIMENT

Figure 1:
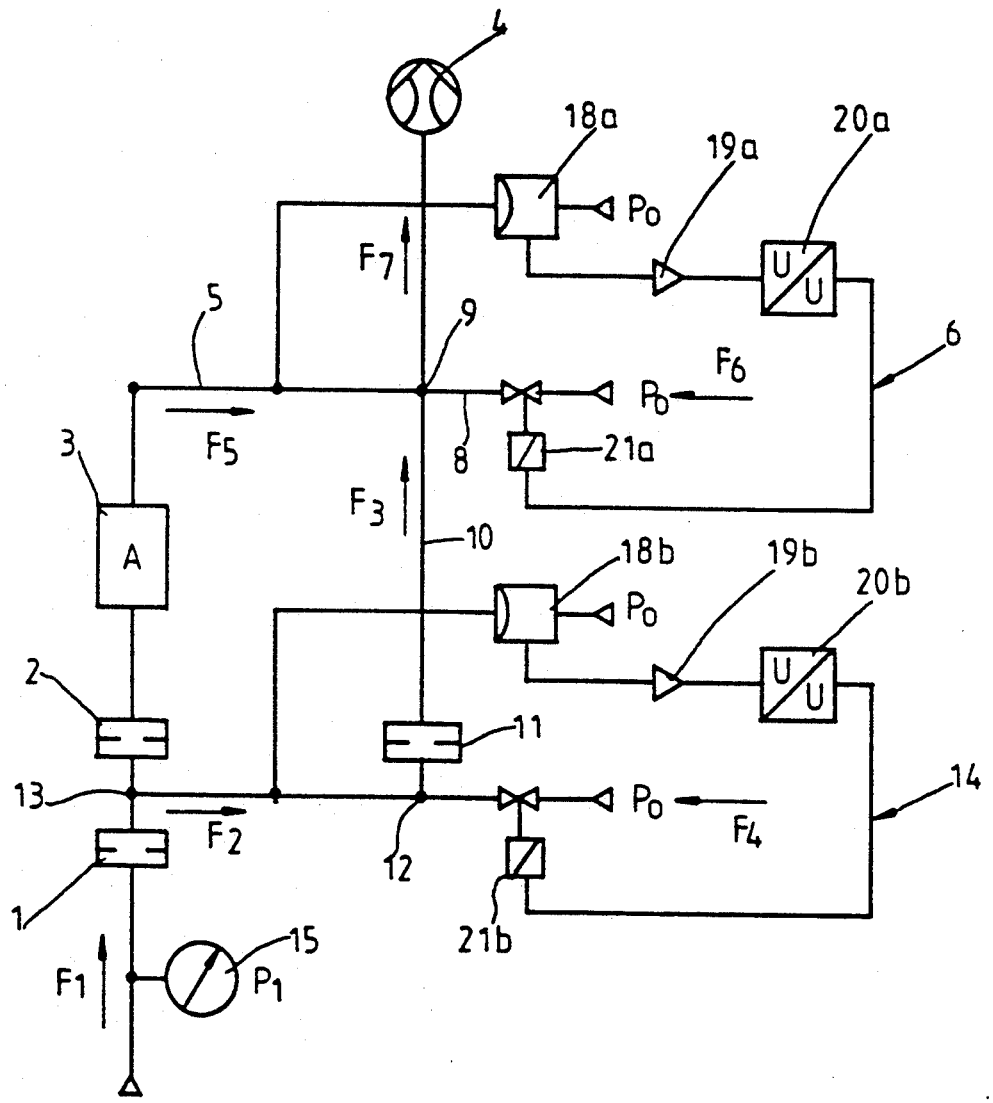

In the following an exemplary embodiment of the invention will be described making reference to the single FIGURE of the drawing. The fundamental construction and mode of operation of the vacuum regulation in a continuously operated gas analyser is explained in detail in U.S. Pat. No. 4,341,108. Reference is expressly made to this specification. The same reference symbols will be used for identical or similar components. The main difference resides in the fact that the vacuum regulation is carried out not using conventional differential pressure regulators but using special electronic regulating circuits 6, 14. Such a regulating circuit comprises a respective piezoelectric pressure sensor 18a, 18b, a measuring amplifier 19a, 19b, a proportional-/integral controller 20a, 20b and an electropneumatic control element 21a, 21b. With the assistance of the piezoelectric sensor 18a, 18b the vacuum is in each case detected in the form of an electric signal, independently of the flow, with an accuracy of ±0.01 mbar. This signal is amplified by the measuring amplifier 19a, 19b and fed to the PI-controller 20a, 20b. The electric output signals of the PI-controllers 20a, 20b act directly upon the electropneumatic control elements 21a and 21b. The PI-controllers 20a, 20b carry out the theoretical/actual value comparison and thereby generate a control signal which controls the electropneumatic control elements 21a, 21b. As a result of this direct driving, a hysteresis-free regulating action and a regulating accuracy of ±0.01 mbar is achieved. By virtue of the special selection and combination of the regulating circuit components, which are particularly well matched to one another, good long-term stability in a temperature range of −10° C. to +70° C. is obtained. A further advantage resides in that via the control signal, i.e. by calling up the control variables, it is possible to monitor both the flow of gas to be measured and the pump efficiency without the need to install additional sensors or flow meters in the gas stream to be measured. The described new vacuum regulating system also ensures that the gas analysis measuring device operates independently of the atmospheric pressure as the two sensors each use the atmospheric pressure as reference pressure, i.e. both use the same reference pressure.

The piezoelectric sensors and the electropneumatic control elements are commercially available components.

I claim:

1. A continuously operated gas analyser comprising a) a detector (3) which is dependent upon the mass flow of the gas to be analyzed, b) a suction device (4) at the detector output, c) a vacuum regulating circuit (6) which is connected to the detector output and which maintains constant the vacuum $p_3$, generated by the suction device (4), at the detector output in relation to the atmospheric pressure $p_o$, d) a first choke (11) which is connected upstream of the detector (3) in the pipe-line for the gas to be measured, e) a second choke (11) which is connected in parallel to the series arrangement of first choke (2) and detector (3) as a by-pass, f) a third choke (11) which is connected upstream of the common gas inlet (12, 13) into the first choke and the second choke, and g) a further vacuum regulating circuit (14) which is connected to the common gas inlet and which maintains constant the pressure $p_2$ prevailing at said connection point in relation to the atmospheric pressure $p_o$, characterized in that the vacuum regulating circuits (6, 14) each comprise a piezoelectric pressure sensor (18a, 18b), a proportional/integral controller (20a, 20b) and an electropneumatic control element (21a, 21b).

* * * * *